United States Patent
Weissman

(10) Patent No.: US 7,365,102 B1
(45) Date of Patent: Apr. 29, 2008

(54) PROCESS FOR PRE-REFORMING HYDROCARBON FUELS

(75) Inventor: Jeffrey G. Weissman, West Henrietta, NY (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 11/710,820

(22) Filed: Feb. 26, 2007

(51) Int. Cl.
*C07C 27/00* (2006.01)

(52) U.S. Cl. ............ 518/700; 518/702; 518/703; 518/704

(58) Field of Classification Search ......... 518/700–704
See application file for complete search history.

(56) References Cited

U.S. PATENT DOCUMENTS

| | | | |
|---|---|---|---|
| 3,642,460 A | 2/1972 | Thompson | |
| 3,882,636 A | 5/1975 | Horie et al. | |
| 3,988,425 A | 10/1976 | Jockel et al. | |
| 4,417,905 A | 11/1983 | Banks et al. | |
| 4,844,837 A | 7/1989 | Heck et al. | |
| 6,335,474 B1 | 1/2002 | Ostberg et al. | |
| 2004/0197240 A1* | 10/2004 | Wheat et al. | 422/105 |
| 2005/0207970 A1 | 9/2005 | Garg et al. | |

FOREIGN PATENT DOCUMENTS

| EP | 1586535 A2 | 10/2005 |
|---|---|---|
| EP | 1616838 A2 | 1/2006 |

OTHER PUBLICATIONS

Meusinger, J., et al.; "Reforming of natural gas in solid oxide fuel cell systems", Journal of Power Sources 71 (1998) 315-320.
Tompsett, G.A., et al.; "Novel applications for micro-SOFCs"; Journal of Power Sources 86 (2000) 376-382.
Sperle, Thomas, et al.; "Pre-reforming of natural gas on a Ni catalyst Criteria for carbon free operation"; Applied Catalysis A: General 282 (2005) 195-204.
Peters, R.; "Pre-reforming of natural gas in solid oxide fuel-cell systems"; Journal of Power Sources, 86 (2000), pp. 432-441.

* cited by examiner

*Primary Examiner*—J. Parsa
(74) *Attorney, Agent, or Firm*—Paul L. Marshall

(57) ABSTRACT

In a process for forming a methane-enriched fuel, a hydrocarbon feedstock that includes hydrocarbons having molecular weights greater than that of methane ($CH_4$) is mixed with an oxidizable gaseous reactant that includes water ($H_2O$) and is free of molecular oxygen ($O_2$). The mixture, which has a $H_2O$/total hydrocarbon ($H_2O/C$) ratio of less than about 1, is heated to an elevated temperature in the presence of a catalyst to form a methane-enriched pre-reformate product. At least a portion of the feedstock hydrocarbons having molecular weights greater than that of methane is converted to methane ($CH_4$) in the process.

15 Claims, No Drawings

PROCESS FOR PRE-REFORMING HYDROCARBON FUELS

GOVERNMENT-SPONSORED STATEMENT

This invention was made with United States Government support under Government Contract/Purchase Order No. DE-FC26-02NT41246. The Government has certain rights in this invention.

TECHNICAL FIELD

The present invention relates to hydrocarbon fuels and, more particularly to a process for pre-reforming hydrocarbon feedstocks to methane-enriched fuels.

BACKGROUND OF THE INVENTION

High-temperature fuel cells operate in an exothermic mode; for example, for solid-oxide fuel cells (SOFC) fueled with reformate, a mixture of primarily CO and $H_2$, heat can be released during transport of oxygen across the solid electrolyte and from reaction of the transported oxygen with CO and $H_2$ fuel. To avoid excessive temperatures that could damage the cell, active cooling is required. The extent of cooling is such that the amount of coolant required is a significant parasitic load on the cell that substantially reduces overall system efficiency.

Through direct fueling of a high-temperature fuel cell with $CH_4$, heat adsorbing endothermic reactions can be introduced. As $CO_2$ and H2O are formed in the cathode, these can react endothermically with $CH_4$ to form additional CO and $H_2$, providing additional fuel to the fuel cell while at the same time serving as a sink for thermal energy. Thus a desirable means of operating high temperature fuel cells is to provide $CH_4$ as the fuel, instead of reformate, and allowing for internal reforming. In this way the parasitic cooling load requirements can be minimized.

However, there is no economic commercial source of methane gas; natural gas is an option. Most natural gases typically contain about 85-95% $CH_4$, non-methane hydrocarbon components such as 1-5% $C_2H_6$, with lesser amounts of higher hydrocarbons, $C_3H_8$, $C_4H_{10}$, $C_5H_{12}$, and so on, plus in some cases $N_2$, He, and $CO_2$. At the conditions typical of high temperature fuel cells, these non-methane hydrocarbon components are well known to form carbonaceous deposits, tars, resins or solids with a very low H/C atom ratio, less than 1, in the anode, especially at the entrance sections of the anode where there can be local deficiencies in $CO_2$ and $H_2O$, as compared to the overall concentrations of these components in the anode portion of the fuel cell. Thus, while a desirable operation of high-temperature fuel cells is to directly fuel the anode with methane-rich natural gas, a means needs to be established to prevent carbonaceous deposits from forming. If natural gas or other hydrocarbon fuels can be converted to substantially pure methane, they can be used directly as fuel for high-temperature fuel cells.

U.S. Patent Publication No. 2005/0207970 Al, the disclosure of which is incorporated herein by reference, and related Patents EP 1586535A2 and EP 1616838 A2 disclose a process for pre-reforming of natural gas using a nickel-based catalyst. The process uses a $H_2O/C$ ratio of 3, and while claimed for natural gas, its utility is demonstrated only for pure methane. Since conversion of methane into nonhydrocarbons is reported, it can be concluded that the H/C ratio of hydrocarbons in the product, as compared to the feed, decreases.

U.S. Pat. No. 6,355,474, the disclosure of which is incorporated herein by reference, describes a process for pre-reforming of natural gas employing a noble metal based catalyst. However, the claimed process requires oxygen and an excessive amount of steam, and is therefore essentially a steam reforming process. While conversion of higher hydrocarbons is reported, a significant amount of methane conversion is also reported.

U.S. Pat. No. 4,844,837, the disclosure of which is incorporated herein by reference, describes a process for partial oxidation of hydrocarbons, essentially a pre-reformer for steam reforming. Catalyst compositions claimed include Pt, Pd, or Rh supported on alumina ($Al_2O_3$) stabilized with ceria ($CeO_2$), lanthana ($La_2O_3$), baria (BaO), or chromia ($Cr_2O_3$). The claimed process requires a $H_2O/C$ ratio of at least 0.35 and an $O_2/C$ ratio of at least about 0.2. U.S. Pat. No. 3,642,460, and similar U.S. Pat. Nos. 4,417,905 and 3,882,636, the disclosures of which are incorporated herein by reference, describe natural gas or hydrocarbon pre-reforming processes, to produce a methane rich product gas. These are all essentially steam reforming processes, requiring excessive amounts of water. Likewise, U.S. Pat. No. 3,988,425, the disclosure of which is incorporated herein by reference, employs a small amount of $H_2$ in addition to steam in the feed, which has a $H_2O/C$ ratio of 1.1-1.7.

*Journal of Power Sources*, 71 (1998), pp 315-320, describes reforming over conventional Raschig ring nickel based steam reforming catalysts, using a $H_2O/C$ ratio of 3. At 3.5 bars, conversions of 41% of $CH_4$ and 73% of $C_2H_6$ were achieved at 1070/hr space velocity (measured at STP) and 690° C. Propane conversion was not measured

*Journal of Power Sources*, 86 (2000), pp 376-382, describes propane or butane fueled solid-oxide fuel cells in which the pre-reforming catalyst is ruthenium on Saffil non-woven alumina-silica (96/4) ceramic wool. The reported pre-reforming reaction is essentially partial oxidation, as the only oxygen-carrying species entering the pre-reformer is air.

*Journal of Power Sources*, 86 (2000), pp 432-441, describes steam reforming, combined steam and $CO_2$ reforming, or simulated anode-tail gas reforming of natural gas using a nickel-based catalyst. In all cases, the feed $H_2O/C$ ratio is maintained at 2.5. For the case of anode tail gas reforming, methane conversions of 10-25% are reported, but there is no report of the conversion of the ethane or propane contents of the natural gas

*Applied Catalysis A*, 282 (2005), pp 195-204, reports pre-reforming of natural gas over a nickel-based catalyst, but the described process is steam reforming at a $H_2O/C$ ratio of from 0.74 to 3.4.

SUMMARY OF THE INVENTION

The present invention is directed to a process for forming a methane-enriched fuel from a hydrocarbon feedstock that comprises forming a mixture of a hydrocarbon feedstock that includes hydrocarbons having molecular weights greater than that of methane ($CH_4$) and an oxidizable gaseous reactant that comprises water ($H_2O$) and is free of molecular oxygen ($O_2$). The mixture, which has a $H_2O$/total hydrocarbon ($H_2O/C$) ratio of less than about 1, is heated to an elevated temperature in the presence of a catalyst to form a methane-enriched pre-reformate product. At least a portion of the feedstock hydrocarbons having molecular weights greater than that of methane is converted to methane ($CH_4$) in the process.

DESCRIPTION OF THE PREFERRED EMBODIMENTS

Pre-reforming is the process of converting non-methane hydrocarbons included in a hydrocarbon feed into methane, which results in an increase in the overall H/C ratio of the hydrocarbon only content of the product relative to the hydrocarbon content of the feed. The goal of pre-reforming is to minimize higher hydrocarbon content while maximizing $CH_4$ content. Suitable hydrocarbon feeds include natural gas, liquefied petroleum gas (LPG), propane, butane, gasoline, ethanol, etc. In the case of natural gas, with an H/C ratio typically of about 3.83, the goal is to produce gas with an H/C ratio of $CH_4$, i.e., 4.0.

In contrast, internal reforming, which includes both direct and indirect internal reforming and is conducted in the anode side of fuel cell stacks, has as its goal the complete conversion of all hydrocarbons, including $CH_4$, into mixtures of CO and $H_2$ for use as fuel for the fuel cell. Likewise, steam reforming, using $H_2O$ as the oxidant at $H_2O$:feed carbon ($H_2O$/C) ratios greater than, more typically greater than 2 or 3; dry reforming, using $CO_2$ as the oxidant; partial oxidation reforming, using purified $O_2$ or air as the oxidant; and combinations of these, referred to as autothermal reforming, all have as their goal the conversion of all hydrocarbons present into nonhydrocarbon containing products, i.e., mixtures of CO and $H_2$. The present invention provides a process for pre-reforming of hydrocarbon feedstocks that comprises mixing a hydrocarbon feedstock such as natural gas, liquefied petroleum gas (LPG), propanes, butanes, naphthas, gasolines, kerosenes, gas-oils, diesel fuels, coal liquids, tar sands or tar sand liquids, and the like, with an oxidizable hydrogen- and oxygen-containing gaseous reactant mixture. The reactant gas has components that are capable of reacting with oxygen; $H_2$ and CO, for example, are capable of reacting with oxygen, while $H_2O$ and $CO_2$, being already fully oxidized, are not. The reacting gas can, for example, be obtained through recycle of fuel cell anode tail gas, in a fuel cell that is operated at less than 100% utilization.

In a typical process, an anode tail gas recycle reactant mixture containing fuel un-utilized by the fuel cell, $H_2$ and CO, fuel cell utilization products $H_2O$ and $CO_2$, un-reformed $CH_4$, and diluents such as $N_2$ or Ar is mixed with the fuel containing non-methane hydrocarbons. This reactant-hydrocarbon fuel mixture is fed to a pre-reforming device that contains a catalyst and may be externally heated by, for example, combustion of a portion of the fuel or a portion of the anode tail-gas mixture. The product of the pre-reforming step is a pre-reformate that contains substantial quantities of the inlet methane and of additional methane obtained by conversion of inlet non-methane hydrocarbons, along with little or no residual non-methane hydrocarbons. This pre-reformate product is fed to the anode side of a high-temperature fuel cell, for example an SOFC, that is operated at about 50-80% utilization so that a portion of the $H_2$ and CO either entering the fuel cell or formed in the fuel cell exits the anode. A suitable device splits the anode tail-gas, a portion being sent to a combustor to provide suitable heat while a portion is recycled, using a combination of heat exchangers, compressors, pumps, turbines, or injectors, to the pre-reformer, where it serves as the hydrogen- and oxygen-containing reactant mixture that includes components capable of reacting with oxygen.

Additional distinguishing features of the pre-reforming process in accordance with the present invention include a gaseous reactant feed comprising reducible gases in an amount of at least about 10%, preferably at least about 20%, up to about 100%. No oxygen ($O_2$), either in its pure form or as a component of air, is present in the reactant feed. Reducible gases include hydrogen ($H_2$) and carbon monoxide (CO).

It is desirable to minimize the water content in the pre-reformer feed, as excessive amounts of water increase the heat load on the pre-reformer and lower its system efficiency. The ratio of water to total hydrocarbon carbon, $H_2O$/C, in the pre-reformer feed is preferably less than about 1, preferably less than about 0.5, more preferably less than about 0.25.

To maintain maximum benefit to the fuel cell operation, conversion of methane should be limited to less than about 40%, preferably less than about 30%, i.e., no more than about 30-40% of the carbon in the hydrocarbon feedstock should be converted into non-methane carbon species such as CO or $CO_2$.

In accordance with the present invention, natural gas is mixed with anode tail gas and passed over a suitable catalyst to yield a pre-reformate product suitable for use in high-temperature fuel cells. For example, a natural gas feed containing 93% $CH_4$, 4.99% $C_2H_6$, and 2.01% $C_3H_8$, is mixed with an anode tail gas containing 10.59% $H_2$, 11.06% CO, 12.96% $CO_2$, 0.40% $CH_4$, 45.07% $N_2$, and 19.92% $H_2O$. The overall H/C ratio of the hydrocarbon content of the pre-reformer feed is 3.83, and its overall $H_2O$/C ratio is 0.178. The reactant feed contains 21.64% reducible gases and is free of $O_2$. The pre-reformer feed, which comprises equal volumetric amounts of natural gas and anode tail gas, is passed over a catalyst, at a space velocity of 52,418 volume of gas per hour per volume of catalyst. The catalyst comprises 2 wt. % Rh on alumina, loaded to 108 g. Rh per cubic foot of substrate, onto a 400 cells-per-square-inch cordierite honeycomb monolithic substrate containing a base coat of alumina.

The results of the test are presented in TABLE 1. At all temperatures, methane conversion was held to less than 30%. At a temperature of 691° C., $C_2H_6$ and $C_3H_8$ conversions of over 55% and 65%, respectively, were obtained, along with a product hydrocarbon H/C ratio of 3.91.

In a similar test, the same process was used, except that the catalyst employed comprised 5 wt. % Ni on an oxide composition of 31.5% $CeO_2$, 58.5% $ZrO_2$, 5% $La_2O_3$, and 5% $Y_2O_3$, loaded to 62 g. Ni per cubic foot of substrate, onto a 400 cells-per-square-inch cordierite honeycomb monolithic substrate containing a base coat of alumina, otherwise at the same process conditions. The results of this test are presented in TABLE 2.

Although the Ni-based catalyst was not as effective as the Rh-based catalyst, the methane conversion was held to less than 22% at all temperatures, while over 30 or 40% conversion of $C_2H_6$ and $C_3H_8$, respectively, at a temperature of 680° C. were obtained, along with a product hydrocarbon H/C ratio that was increased to 3.87, compared to 3.83 present in the feed hydrocarbon natural gas.

In a further test, a catalyst containing 2 wt. % Rh on an oxide composition of 31.5% $CeO_2$, 58.5% $ZrO_2$, 5% $La_2O_3$, and 5% $Y_2O_3$, loaded to 56 g. Rh per cubic foot of substrate, onto a 400 cells-per-square-inch cordierite honeycomb monolithic substrate containing a base coat of alumina, was employed under the same process conditions as previously described, except that in some instances the space velocity was varied. The results of this test are presented in TABLE 3. At the higher space velocities, conversions and hydrocarbon product H/C ratios were similar to the prior test with rhodium catalysts. Decreasing space velocity to about 37,000 or 21,500/hr resulted in a small increase in methane conversion, but close to 100% conversion of both $C_2H_6$ and $C_3H_8$, with the H/C of the hydrocarbon product close to that of methane, 4.

Additional testing shows that only a suitable combination of space velocities, reactant to fuel ratios, and temperatures will meet the required process constraints. For example, operating at too low a space velocity may result in too much methane conversion. Operating at too high a reactant gas to hydrocarbon ratio may also result in too much methane conversion; this can be overcome by operating at lower temperatures, higher space velocities, or a less active catalyst.

In a test similar to those described above, a catalyst containing 2 wt. % Rh on an oxide composition of 40.0% $CeO_2$, 50.0%, $ZrO_2$, and 5% $La_2O_3$, loaded onto a 400 cells-per-square-inch cordierite honeycomb monolithic substrate containing a base coat of alumina was heated at 766° C. the space velocity was lowered to 33,211/hr, and the inlet $H_2O/C$ was increased to 0.501. Under these conditions, although $C_2H_6$ and $C_3H_8$ conversions were almost 100%, methane conversion reached 85%, indicating that a combination of lower space velocities and higher $H_2O/C$ ratios is not suitable for this process.

TABLE 1

Pre-reformate product composition using a rhodium-based catalyst

| Temperature (° C.) | SV (/hr) | $CH_4$ conv. | $C_2H_6$ conv. | $C_3H_8$ conv. | HC out H/C |
|---|---|---|---|---|---|
| 375 | 52418 | 0.253 | 0.270 | 0.345 | 3.84 |
| 450 | 52418 | 0.252 | 0.268 | 0.343 | 3.84 |
| 520 | 52418 | 0.250 | 0.268 | 0.352 | 3.85 |
| 590 | 52418 | 0.249 | 0.286 | 0.373 | 3.85 |
| 691 | 52418 | 0.218 | 0.555 | 0.667 | 3.91 |
| 771 | 52418 | 0.251 | 0.451 | 0.632 | 3.89 |

Temperature measured at catalyst radial and axial center point.
SV: space velocity.
Conversion (conv.) is defined as 1 − (volumetric product flow rate)/(volumetric feed flow rate) of the specific component.

TABLE 2

Pre-reformate product composition using a nickel-based catalyst

| Temperature (° C.) | SV (/hr) | $CH_4$ conv. | $C_2H_6$ conv. | $C_3H_8$ conv. | HC out H/C |
|---|---|---|---|---|---|
| 365 | 51838 | 0.178 | 0.196 | 0.272 | 3.84 |
| 465 | 51838 | 0.213 | 0.217 | 0.297 | 3.84 |
| 572 | 51838 | 0.212 | 0.224 | 0.305 | 3.84 |
| 640 | 51838 | 0.211 | 0.233 | 0.320 | 3.85 |
| 680 | 51838 | 0.210 | 0.333 | 0.446 | 3.87 |

TABLE 3

Pre-reformate product composition using a rhodium-based catalyst

| Temperature (° C.) | SV (/hr) | $CH_4$ conv. | $C_2H_6$ conv. | $C_3H_8$ conv. | HC out H/C |
|---|---|---|---|---|---|
| 303 | 52418 | 0.249 | 0.245 | 0.322 | 3.84 |
| 402 | 52418 | 0.249 | 0.243 | 0.321 | 3.84 |
| 508 | 52418 | 0.222 | 0.367 | 0.517 | 3.87 |
| 566 | 52418 | 0.221 | 0.463 | 0.600 | 3.89 |
| 588 | 52418 | 0.227 | 0.568 | 0.749 | 3.92 |
| 615 | 36692 | 0.249 | 0.719 | 0.882 | 3.95 |
| 628* | 21547 | 0.312 | 0.889 | 0.993 | 3.98 |

*operated at total inlet of $H_2O/C$ of 0.223; others were at 0.178

While the invention has been described by reference to various specific embodiments, it should be understood that changes may be made within the spirit and scope of the inventive concepts described. Accordingly, it is intended that the invention not be limited to the described embodiments, but will have full scope defined by the language of the following claims.

What is claimed is:

1. A process for forming a methane-enriched fuel from a hydrocarbon feedstock, said process comprising:
    forming a mixture of a hydrocarbon feedstock that includes hydrocarbons having molecular weights greater than that of methane ($CH_4$) and an oxidizable gaseous reactant that comprises water ($H_2O$) and is free of molecular oxygen ($O_2$), said mixture having a $H_2O$/total hydrocarbon ($H_2O/C$) ratio of less than 1; and
    heating said mixture to an elevated temperature in the presence of a catalyst to form a methane-enriched pre-reformate product;
    whereby at least a portion of said hydrocarbons having molecular weights greater than that of methane is converted to methane ($CH_4$).

2. The process of claim 1 wherein said mixture has a $H_2O$/total hydrocarbon ($H_2O/C$) ratio of less than 0.5.

3. The process of claim 2 wherein said mixture has a $H_2O$/total hydrocarbon ($H_2O/C$) ratio of less than 0.25.

4. The process of claim 1 wherein said hydrocarbon feedstock is selected from the group consisting of natural gas, liquefied petroleum gas (LPG), propanes, butanes, naphthas, gasolines, kerosenes, gas-oils, diesel fuels, coal liquids, tar sands, tar sand liquids, and mixtures thereof.

5. The process of claim 1 wherein said gaseous reactant comprises hydrogen ($H_2$) and carbon monoxide (CO).

6. The process of claim 1 wherein said gaseous reactant comprises anode tail gas from a fuel cell.

7. The process of claim 1 wherein said gaseous reactant comprises at least about 10% reducible gases.

8. The process of claim 7 wherein said gaseous reactant comprises at least about 20% reducible gases.

9. The process of claim 1 wherein said catalyst comprises rhodium (Rh).

10. The process of claim 1 wherein said catalyst comprises nickel (Ni).

11. The process of claim 1 wherein said elevated temperature is about 500° C. to 700° C.

12. The process of claim 1 wherein said methane-enriched pre-reformate product has a hydrogen/carbon (H/C) ratio of at least 3.85.

13. The process of claim 12 wherein said methane-enriched pre-reformate product has a hydrogen/carbon (H/C) ratio of at least 3.90.

14. The process of claim 1 wherein no more than about 40% of carbon present in said hydrocarbon feedstock is converted into non-methane carbon species.

15. The process of claim 14 wherein no more than about 30% of carbon present in said hydrocarbon feedstock is converted into non-methane carbon species.

* * * * *